(12) United States Patent
Pallisgaard

US010227655B2

(10) Patent No.: US 10,227,655 B2
(45) Date of Patent: Mar. 12, 2019

(54) METHOD FOR ANALYZING BODY FLUID SAMPLES

(71) Applicant: Region Syddanmark, Vejle (DK)

(72) Inventor: Niels Pallisgaard, Odense M (DK)

(73) Assignee: REGION SYDDANMARK, Vejle (DK)

( * ) Notice: Subject to any disclaimer, the term of this patent is extended or adjusted under 35 U.S.C. 154(b) by 314 days.

(21) Appl. No.: 15/032,983

(22) PCT Filed: Oct. 29, 2014

(86) PCT No.: PCT/EP2014/073170
§ 371 (c)(1),
(2) Date: Apr. 28, 2016

(87) PCT Pub. No.: WO2015/063121
PCT Pub. Date: May 7, 2015

(65) Prior Publication Data
US 2016/0281169 A1 Sep. 29, 2016

(30) Foreign Application Priority Data

Oct. 29, 2013 (DK) .......................... PA 2013 70628
Oct. 30, 2013 (DK) .......................... PA 2013 70634

(51) Int. Cl.
*C12P 19/34* (2006.01)
*C12Q 1/6886* (2018.01)
*C12Q 1/6881* (2018.01)

(52) U.S. Cl.
CPC ......... *C12Q 1/6886* (2013.01); *C12Q 1/6881* (2013.01); *C12Q 2600/158* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 8,148,067 B2* | 4/2012 | Lal | C12Q 1/6809 435/6.1 |
| 8,859,748 B2* | 10/2014 | Van Dongen | C12Q 1/6886 435/6.12 |
| 2009/0280479 A1* | 11/2009 | Hoon | C12Q 1/6886 435/6.12 |
| 2010/0124743 A1 | 5/2010 | Nagaoka | |
| 2013/0012405 A1 | 1/2013 | Duttagupta et al. | |

FOREIGN PATENT DOCUMENTS

| CN | 102605070 | 7/2012 |
| EP | 1712639 | 10/2006 |
| WO | 1997046706 | 12/1997 |
| WO | 2004033728 | 4/2004 |
| WO | 2005054506 | 6/2005 |
| WO | 2006128192 | 11/2006 |
| WO | 2006138443 | 12/2006 |
| WO | 2011051495 | 5/2011 |
| WO | 2012028746 | 3/2012 |
| WO | 2013128204 | 9/2013 |

OTHER PUBLICATIONS

Rychlik et al., Nucleic Acids Research 17(21), 8543-8551 (Year: 1989).*
Dawson et al, "Analysis of Circulating Tumor DNA to Monitor Metastatic Breast Cancer," The New England Journal of Medicine, vol. 368, pp. 1199-1209 (2013).
Fatouros et al., Cell-Free Plasma DNA as a Novel Marker of Aseptic Inflammation Severity Related to Exercise Overtraining, Clinical Chemistry, vol. 52, No. 9, pp. 1820-1824 (2006).
Goebela et al., "Circulating Nucleic Acids in Plasma or Serum (CNAPS) as a Prognostic and Predictive Markers in Patients with Solid Neoplasias," Disease Markers, vol. 21, pp. 105-120 (2005).
Spindler et al., "Quantitative Cell-Free DNA, KRAS, and BRAF Mutations in Plasma from Patients with Metastatic Colorectal Cancer During Treatment with Cetuximab an Irinotecan," Clinical Cancer Research, vol. 18, No. 4, pp. 1177-1185 (2012).
Jahr et al., "DNA Fragments in the Blood Plasma of Cancer Patients: Quantitations and Evidence for Their Origin from the Apoptotic and Necrotic Cells," Cancer Research, vol. 61, pp. 1659-1665 (2001).
Schwarz et al, "Quantification of Free Total Plasma DNA and Minimal Residual Disease Detection in the Plasma of Children with Acute Lymphoblastic Leukemia," Annals of Hematology, vol. 88, pp. 897-905 (2009).
Fleischhacker et al., "Circulating Nucleic Acids (CNAs) and Cancer—A Survey," Biochimica et Biophysica Acta, vol. 1775, pp. 181-232 (2007).
Van Der Velden et al., "Immunoglobulin Light Chain Gene Rearrangements in Precursor-B-acute Lymphoblastic Leukemia: Characteristics and the Applicability for the Detection of Minimal Residual Disease," The Hematology Journal, vol. 91, No. 5, pp. 679-682 (2006).
Van Der Velden et al., "Analysis of Minimal Residual Disease by Ig/TCR Gene Rearrangements: Guidelines for Interpretation of Real-Time Quantitative PCR Data," Leukemia, vol. 21, pp. 604-611 (2007).

(Continued)

*Primary Examiner* — Kenneth R Horlick
(74) *Attorney, Agent, or Firm* — Fisherbroyles, LLP

(57) ABSTRACT

Methods and kits for qualifying the analysis of cell free DNA in e.g. plasma and serum samples are provided, based on the identification of contaminating DNA from B lymphocytes. Quantitative PCR (qPCR) can be used to detecting or determining the level of clonally rearranged immunoglobulin heavy-chain (IGH) genes, immunoglobulin kappa chain (IGK) genes, or immunoglobulin lambda-chain (IGL) genes, or a combination of any thereof. Samples identified as containing contaminating DNA can thus be identified and excluded or corrected, improving the accuracy of cf DNA determinations as a diagnostic, prognostic and treatment monitoring tool.

Figure 1:
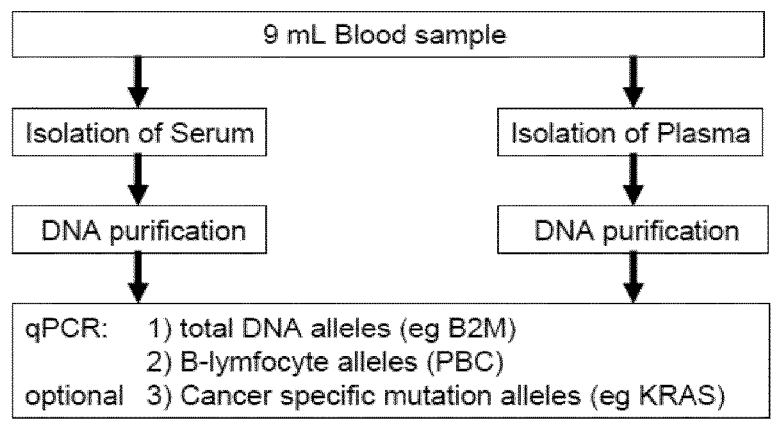

8 Claims, 2 Drawing Sheets
Specification includes a Sequence Listing.

(56) References Cited

OTHER PUBLICATIONS

Van Dogen et al., 'Design and Standardization of PCR Primers and Protocols for Detection of Clonal Immunoglobulin and T-Cell Receptor Gene Recombinations in Suspect Lymphoproliferations: Report of the BIOMED-2 concerted Action BMH4-CT98-3936, Leukemia, vol. 17, pp. 2257-2317 (2003).

Ivancic-Jelecki et al., Isolation of Cell-Free DNA from plasma by Chromatography on Short Monolithic Columns and Quantification of Non-Apoptotic Fragments by Real-Time Polymerase Chain Reaction, Journal of Chromatography A, vol. 1216, pp. 2717-2724 (2009).

Dydensborg et al., "Normalizing genes for quantitative RT-PCR in differentiating human intestinal epithelial cells and adenocarcinomas of the colon," American Journal of Physiology. Gastrointestinal and Liver Physiology, vol. 290, pp. G1067-G1074 (2006).

Zhong et al., "Better Detection of Ig Heavy Chain and TCRγ Gene Rearrangement in Plasma Cell-Free DNA from Patients with Non-Hodgkin Lymphoma," Neoplasma, vol. 57, No. 6 pp. 507-511 (2010).

Spence et al., "Demonstration of Array-Based Analysis for Highly Multiplexed PCR Assays," The Journal of Molecular Diagnostics, vol. 13, No. 3 (2011).

Messaoudi et al., "Circulating Cell Free DNA: Preanalytical Considerations," Clinica Chima Acta, Issue 424, pp. 222-230 (2013).

Jung et al., "Cell-Free DNA in the Blood as a Solid Tumor Biomarker—A Critical Appraisal of the Literature," Clinica ahimica Acta, Issue 411, pp. 1611-1624 (2010).

Fleischhacker et al., "Free Circulating Nucleic Acids in Plasma and Serum (CNAPS)—Useful for the Detection of Lung Cancer Patients?", Cancer Biomarkers, Issue 6, pp. 211-219 (2010).

Elshimali et al., "The Clinical Utilization of Circulating Cell Free DNA (CCFDNA) in Blood of Cancer Patients," International Journal of Molecular Science, vol. 14, pp. 18925-18958 (2013).

* cited by examiner

SEQUENCE LISTING

```
<160> NUMBER OF SEQ ID NOS: 27

<210> SEQ ID NO 1
<211> LENGTH: 29
<212> TYPE: DNA
<213> ORGANISM: Artificial
<220> FEATURE:
<223> OTHER INFORMATION: Primer

<400> SEQUENCE: 1
taaaacttaa tgtcttcctt tttttctc                                     29

<210> SEQ ID NO 2
<211> LENGTH: 26
<212> TYPE: DNA
<213> ORGANISM: Artificial
<220> FEATURE:
<223> OTHER INFORMATION: Probe

<400> SEQUENCE: 2
cctccatgat gctgcttaca tgtctc                                       26

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
aaacattttc tcaaggtcaa aaactta                                      27

<210> SEQ ID NO 4
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(17)
<223> OTHER INFORMATION: C or T

<400> SEQUENCE: 4
atctgcaaat gaacagnctg aga                                          23

<210> SEQ ID NO 5
<211> LENGTH: 28
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (2)..(2)
<223> OTHER INFORMATION: C or T
<220> FEATURE:
```

```
<221> NAME/KEY: misc_feature
<222> LOCATION: (11)..(11)
<223> OTHER INFORMATION: A or G

<400> SEQUENCE: 5
cngaggacac ngctgtgtat tactgtgc                                              28

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
cttacctgag gagacggtga c                                                     21

<210> SEQ ID NO 7
<211> LENGTH: 25
<212> TYPE: DNA
<213> ORGANISM: Artificial
<220> FEATURE:
<223> OTHER INFORMATION: Probe

<400> SEQUENCE: 7
accctggtca ccgtctcctc aggtg                                                 25

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
cgctatcccc agacagcaga                                                       20

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ggtgcctgga cagagaagac t                                                     21

<210> SEQ ID NO 10
<211> LENGTH: 26
<212> TYPE: DNA
<213> ORGANISM: Artificial
<220> FEATURE:
<223> OTHER INFORMATION: Primer

<400> SEQUENCE: 10
cagagttaaa gcaggagaga ggttgt                                                26

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
agagaggggg tggtgaggac t                                                     21
```

```
<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
gagctgagca gcctgagatc tga                                             23

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
caatgaccaa catggaccct gtgga                                           25

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
tctgcaaatg aacagcctga gagcc                                           25

<210> SEQ ID NO 15
<211> LENGTH: 19
<212> TYPE: DNA
<213> ORGANISM: Artificial
<220> FEATURE:
<223> OTHER INFORMATION: Primer

<400> SEQUENCE: 15
gctctgtgac cgccgcgga                                                  19

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
cagcaccgcc tacctgcagt ggagc                                           25

<210> SEQ ID NO 17
<211> LENGTH: 25
<212> TYPE: DNA
<213> ORGANISM: Artificial
<220> FEATURE:
<223> OTHER INFORMATION: Primer

<400> SEQUENCE: 17
gttctccctg cagctgaact ctgtg                                           25

<210> SEQ ID NO 18
<211> LENGTH: 23
<212> TYPE: DNA
<213> ORGANISM: Artificial
<220> FEATURE:
```

<223> OTHER INFORMATION: Primer

<400> SEQUENCE: 18
agcacggcat atctgcagat cag                                    23

<210> SEQ ID NO 19
<211> LENGTH: 25
<212> TYPE: DNA
<213> ORGANISM: Artificial Sequence
<220> FEATURE:
<223> OTHER INFORMATION: DNA primer

<400> SEQUENCE: 19
cagcctgcag cctgaagatt ttgca                                  25

<210> SEQ ID NO 20
<211> LENGTH: 25
<212> TYPE: DNA
<213> ORGANISM: Artificial Sequence
<220> FEATURE:
<223> OTHER INFORMATION: DNA primer

<400> SEQUENCE: 20
atgctgagga tgttggggtt tattg                                  25

<210> SEQ ID NO 21
<211> LENGTH: 20
<212> TYPE: DNA
<213> ORGANISM: Artificial Sequence
<220> FEATURE:
<223> OTHER INFORMATION: DNA primer

<400> SEQUENCE: 21
tttgatctcc accttggtcc                                        20

<210> SEQ ID NO 22
<211> LENGTH: 22
<212> TYPE: DNA
<213> ORGANISM: Artificial Sequence
<220> FEATURE:
<223> OTHER INFORMATION: DNA primer

<400> SEQUENCE: 22
ggacagattt cactctcacc at                                     22

<210> SEQ ID NO 23
<211> LENGTH: 20
<212> TYPE: DNA
<213> ORGANISM: Artificial Sequence
<220> FEATURE:
<223> OTHER INFORMATION: DNA primer

<400> SEQUENCE: 23
catgctgaaa tcaggaggat                                        20

<210> SEQ ID NO 24
<211> LENGTH: 23
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (13)..(13)
<223> OTHER INFORMATION: A or G

<400> SEQUENCE: 24

```
tgccagtcct atnacagcag cct                                               23
```

<210> SEQ ID NO 25
<211> LENGTH: 19
<212> TYPE: DNA
<213> ORGANISM: Artificial Sequence
<220> FEATURE:
<223> OTHER INFORMATION: DNA primer

<400> SEQUENCE: 25

```
ctaggacggt cagcttggt                                                    19
```

<210> SEQ ID NO 26
<211> LENGTH: 23
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (16)..(16)
<223> OTHER INFORMATION: C or T

<400> SEQUENCE: 26

```
ggctgnggat gaggcnaatt att                                               23
```

<210> SEQ ID NO 27
<211> LENGTH: 23
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (16)..(16)
<223> OTHER INFORMATION: C or T

<400> SEQUENCE: 27

```
ggctgnggat gaggcngatt att                                               23
```

METHOD FOR ANALYZING BODY FLUID SAMPLES

CROSS-REFERENCE TO RELATED APPLICATIONS

This application is a 35 U.S.C. § 371 US National Phase of International Patent Application No. PCT/EP2014/073170, filed Oct. 29, 2014 and incorporated herein by reference in its entirety, which claims the benefit of Danish Patent Application No. DK PA 2013 70634, filed Oct. 30, 2013 and Danish Patent Application No. DK PA 2013 70628, filed Oct. 29, 2013 which are each incorporated herein by reference in their entireties.

INCORPORATION OF SEQUENCE LISTING

A computer readable form of the sequence listing named "19695pct00-sequence listing.txt", which is 5,395 bytes (measured in operating system MS-Windows), created on Apr. 26, 2016, is electronically filed herewith and is incorporated herein by reference in its entirety. This sequence listing consists of SEQ ID Nos: 1-27.

FIELD OF THE INVENTION

The present invention relates to a method of testing or determining the suitability of a body fluid sample for cell-free DNA analysis, and kits suitable for use in such a method.

BACKGROUND OF THE INVENTION

The blood and other body fluids contain free circulating DNA, also known as cell-free DNA (cfDNA). In cancer patient the amount of cfDNA in plasma and serum samples can be elevated a 1000-fold or more. The level of cfDNA can thus be used both as a diagnostic and prognostic marker for cancer as well as a marker for monitoring the response of the tumor to treatment (Fleischhacker and Schmidt, Cancer Biomark. 2010; 6(3-4):211-9; Goebela et al., Disease Markers 2005; 21:105-120). In addition, the cfDNA of an individual suffering from or at risk for cancer can be analyzed for the presence of known tumor-specific markers, aiding in the diagnosis, staging and prognosis of the disease (Spindler et al., Clin Cancer Res 2012; 18:1177-1185; European Patent 1 712 639 B1; Dawson et al., N Engl 3 Med. 2013; 368(13):1199-209). Analysis of cell-free fetal DNA present in maternal blood provides a method of non-invasive prenatal diagnosis of the fetus, and circulating free plasma DNA has been implicated in conditions associated with tissue injury, including exercise-induced inflammation, and thus is a potential marker for athletic overtraining (Fatouous et al., Clin Chem 2006; 52(9):1820-4).

Since the concentration of cfDNA may, however, be very low, including controls for pre-analytical pitfalls are of utmost importance. One particular problem is that the plasma and serum samples may become contaminated with cellular DNA from blood cells, typically lymphocytes, ruptured during or after the taking of the sample. For example, hemolysis may occur during drawing of the blood sample as a result of the pressure drop from vein to the collection tube, and the cells may lyse during prolonged storage times prior to isolating plasma or serum or because of profound pipetting when isolating the supernatant. Whatever the reason, the cfDNA is then contaminated with DNA from lysed lymphocytes, resulting in falsely increased levels of cfDNA. This increases the risk for, e.g., false positive results when comparing the level of cfDNA to a control value. Contamination may also introduce other errors, such as falsely low levels when monitoring for a cancer-specific mutation and normalizing its level to the total cfDNA in the sample.

U.S. 2010/0124743 A1 relates to a method of diagnosing cancer based on analysis of free DNA in plasma where the measured level of free DNA is compared to first and second threshold values, with the second threshold value being the highest one. If the free DNA is higher than the second threshold value, it is determined that the plasma free DNA is contaminated by normal cell-derived DNA from, e.g., lymphocytes.

WO 2006/128192 relates to the use of cfDNA for diagnosing cancer based on analysis of ALU and LINE repeats in serum. The problems of loss of DNA and contamination by DNA released from cells present in the blood are addressed by eliminating unnecessary purification steps.

US 2013/0012405 A1 relates to methods for diagnosing e.g. cancer by screening for biomarkers in circulating micro-RNAs. Finding that the measurements were frequently confounded by cellular miRNAs of different hematopoietic origin, cellular miRNA signatures were catalogued and analyzed.

Jahr et al. (2001) describes the quantification of the fraction of plasma DNA derived from tumor cells by quantitative methylation-specific PCR, and analyses the possible origins of non-tumor DNA in blood. They considered the possibility that degenerating tumor-infiltrating T lymphocytes contributed to the DNA levels in blood, and therefore quantified the presence of T-cell DNA in plasma samples by PCR amplification of a region the T-cell receptor beta-chain, which exhibits a somatic rearrangement by VDJ recombination.

Ivancic-Jelecki et al. (2009) describes a method for DNA isolation by using anion-exchange chromatography and its use in determining the concentration of contaminating DNA in plasma.

Despite these advances in the art, there is still a need for a control analysis enabling identification of serum and plasma samples comprising contaminating DNA from normal blood cells.

SUMMARY OF THE INVENTION

The invention is based, at least in part, upon the unexpected discovery that the detection and, optionally, quantification of rearranged immunoglobulin genes in body fluid samples can identify samples where the cfDNA is contaminated with DNA from lymphocytes such as B cells. This discovery provides for methods and kits that can be used to qualify the analysis of cell free DNA in e.g., blood, typically in plasma and serum, where the risk for contamination is significant.

So, in a first aspect the present invention relates to a method of assessing whether a body fluid sample is suitable for quantifying or analyzing cell-free DNA (cfDNA) by detecting or determining a level of clonally rearranged immunoglobulin heavy-chain (IGH) genes, immunoglobulin kappa (IGK) genes, immunoglobulin lambda (IGL) genes, or a combination of any thereof. Advantageously, this analysis is performed using quantitative Polymerase Chain Reaction (qPCR), optionally using degenerate primers and/or a mix of primer sets.

In a second aspect, the present invention relates to a method of evaluating whether a body fluid sample derived from a blood sample from a subject is contaminated with cfDNA from B lymphocytes lysed in the blood sample, the method comprising detecting or determining a level of clonally rearranged IGH genes, IGK genes, IGL genes, or a combination of any thereof.

In a third aspect, the invention relates to a kit for analyzing cfDNA in a body fluid sample derived from a blood sample from a subject suffering from or at risk for a cancer, comprising a PCR primer set amplifying clonally rearranged IGH, IGK and/or IGL genes in the body fluid sample. Optionally, the kit further comprises one or more PCR primer sets for amplifying at least one tumor marker gene associated with the cancer.

In a fourth aspect, the invention relates to a kit for use in analyzing whether the cfDNA in a body fluid sample derived from a blood sample is contaminated with DNA derived from B lymphocytes in the blood sample, comprising a PCR primer set selected from the group consisting of (i) SEQ ID NOS:4 and 6, (ii) SEQ ID NOS:15 and 11, (iii) SEQ ID NOS:12 and 11, (iv) SEQ ID NOS:14 and 11, (v) a combination of (ii) to (iv), and (vi) a combination of any two or more of (i) to (iv).

In a fourth aspect, the invention relates to the use of one or more primer sets specific for rearranged IGH genes in a method for determining whether a plasma or serum sample derived from a blood sample is contaminated with cfDNA from lymphocytes lysed in the process of preparing the plasma or serum sample from the blood sample.

These and other aspects and embodiments are described in further detail below.

LEGENDS TO THE FIGURES

FIG. 1 shows the general steps of a typical cfDNA analysis, starting from the taking of a blood sample and including a step of determining whether the extracted cfDNA is contaminated with B cell DNA (here represented by "B lymphocyte alleles (PBC)"). The indicated details such as the amount of blood sample and the inclusion and/or identity of a normalizing gene or a cancer-specific gene provided by way of example only.

Figure 2:
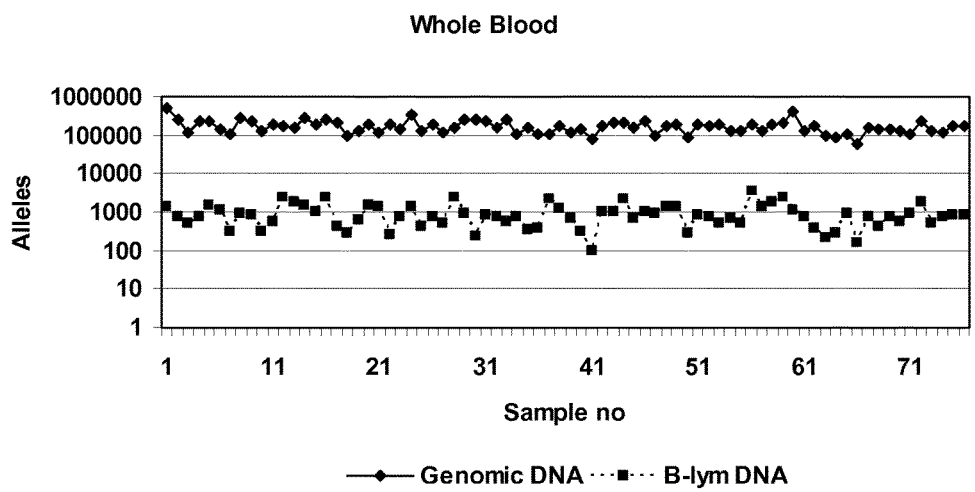

FIG. 2 shows the numbers of genomic alleles and B cell alleles in whole blood samples from normal donors, respectively determined using B2M and IGH rearrangement ("PBC") analysis. For more details, see Example 1.

Figure 3:
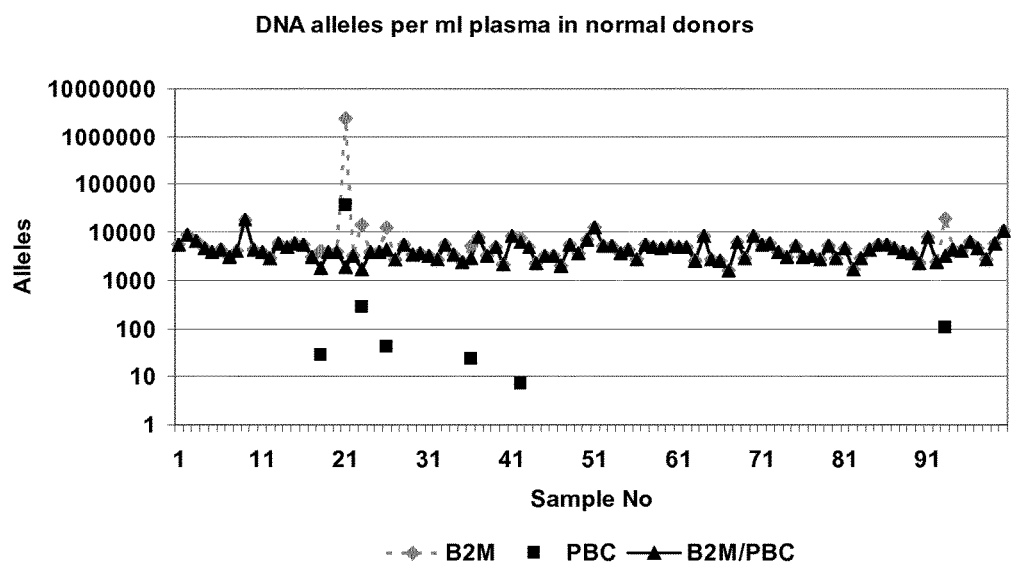

FIG. 3 shows the number of genomic alleles and B cell alleles in plasma from normal donors, respectively determined using B2M and IGH rearrangement ("PBC") analysis. The B2M/PBC ratio is also shown, for each plasma sample. For more details, see Example 1.

Figure 4:
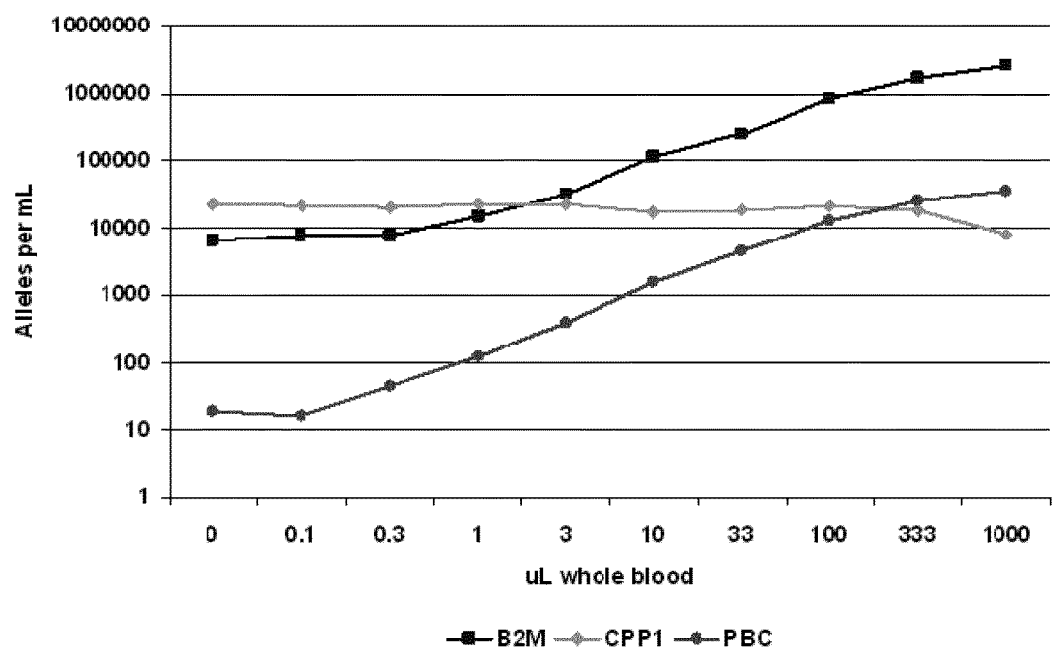

FIG. 4 shows the analysis of plasma samples spiked with whole blood in 3.3 fold increments from 0.1 µL to 1000 µL. A 182 base pair exogenous internal CPP1 control DNA fragment was added, DNA purified and analyzed by qPCR using the B2M (total genomic alleles), PBC (B-cell alleles) and CPP1 (purification control).

DETAILED DISCLOSURE OF THE INVENTION

As described in the Examples, lymphocyte DNA contaminating plasma samples could be identified by a multiplex qPCR assay, detecting a substantial fraction of the unique immunoglobulin DNA rearrangements in B-cells. The present invention thus provides various PCR-based methods, kits and uses for identifying a body fluid sample, typically derived from blood, where the cfDNA is contaminated by B cell DNA. Identifying a contaminated sample allows for its correction (i.e., by removing the contaminant B cell DNA) or exclusion from the diagnostic procedure in question, optionally replacing it with a new body fluid sample from the subject.

So, in a fifth aspect, the invention relates to a method of determining whether a body fluid sample derived from a blood sample from a subject is suitable for quantifying cell-free DNA (cfDNA), comprising (i) performing a quantitative Polymerase Chain Reaction (qPCR) on a body fluid sample derived from a blood sample to determine a level of clonally rearranged genes selected from immunoglobulin heavy-chain (IGH) genes, immunoglobulin kappa (IGK) genes, immunoglobulin lambda (IGL) genes, and a combination of any thereof; and (ii) identifying the body fluid sample as unsuitable for quantifying cfDNA if the level of clonally rearranged genes exceeds a control value.

In a sixth aspect, the invention relates to a method of evaluating whether a body fluid sample derived from a blood sample from a subject is contaminated with cfDNA from B lymphocytes lysed in the blood sample, comprising (i) performing a quantitative Polymerase Chain Reaction (qPCR) on a body fluid sample derived from a blood sample to determine a level of clonally rearranged genes selected from IGH genes, IGK genes, IGL genes, and a combination of any thereof; and (ii) identifying the body fluid sample as contaminated with cfDNA from B lymphocytes if the level of clonally rearranged genes exceeds a control value.

In a preferred embodiment of any of the preceding aspects, the level of clonally rearranged genes comprises a level of IGH genes. In one embodiment of any of the preceding aspects or embodiments, the qPCR is performed with at least one primer pair selected from (i) SEQ ID NOS:4 and 6; (ii) SEQ ID NOS:15 and 11, (iii) SEQ ID NOS:12 and 11, (iv) SEQ ID NOS:14 and 11, (v) a combination of (ii) to (iv), and (vi) a combination of any two or more of (i) to (iv). In one embodiment of any of the preceding aspects or embodiments, the qPCR is performed with primer pairs comprising SEQ ID NOS:4 and 6, optionally wherein the qPCR is performed with a reporter probe comprising SEQ ID NO:5.

The control value of any preceding aspect or embodiment may, for example, be selected from (i) about 0.1% or less of the actual or predicted level of a normalizing gene; (ii) about 20 alleles or less per mL body fluid if the subject is not known to have a condition associated with elevated cfDNA levels; (iii) about 100 alleles or less per mL if the subject is known to have a condition associated with elevated cfDNA levels. Optionally, the control value is a predetermined value.

The qPCR of any preceding aspect or embodiment may also comprise determining the level of a normalizing gene in the body fluid sample.

The body fluid sample of any preceding aspect or embodiment may, for example, be derived from the blood sample by (i) preparing a cell-free fraction of the blood and, optionally (ii) purifying DNA from the cell-free fraction, thereby obtaining the body fluid sample. In a preferred embodiment of any preceding aspect or embodiment, the body fluid is plasma or serum.

In one embodiment of any preceding aspect or embodiment, the subject is at risk for or suffering from cancer. In such embodiments, the qPCR may further comprise determining the level of a tumor marker gene in the body fluid sample.

In a seventh aspect, the invention relates to a kit for analyzing cfDNA in a body fluid sample derived from a blood sample from a subject suffering from or at risk for a cancer, comprising (i) a PCR primer set amplifying clonally rearranged genes in a sample, the clonally rearranged genes selected from IGH genes, IGK genes, IGL genes, and a combination of any thereof, (ii) a PCR primer set for amplifying at least one tumor marker gene associated with the cancer; and optionally, (iii) a reporter probe, a DNA polymerase, a buffer or a set of dNTPs, or a combination of any thereof.

In one embodiment, the PCR primer set of the kit comprises primers sets selected from the group consisting of (i) SEQ ID NOS:4 and 6, (ii) SEQ ID NOS:15 and 11, (iii) SEQ ID NOS:12 and 11, (iv) SEQ ID NOS:14 and 11, (v) a combination of (ii) to (iv), and (vi) a combination of any two or more of (i) to (iv).

In an eighth aspect, the invention relates to a kit for use in analyzing whether the cfDNA in a body fluid sample derived from a blood sample is contaminated with DNA derived from B lymphocytes in the blood sample, comprising a PCR primer set selected from the group consisting of (i) SEQ ID NOS:4 and 6, (ii) SEQ ID NOS:15 and 11, (iii) SEQ ID NOS:12 and 11, (iv) SEQ ID NOS:14 and 11, (v) a combination of (ii) to (iv), and (vi) a combination of any two or more of (i) to (iv); and optionally, at least one of a reporter probe, a DNA polymerase, a buffer and a set of dNTPs.

In one embodiment, the kit of any preceding aspect or embodiment comprises a reporter probe comprising SEQ ID NO:5 or SEQ ID NO:7, or two reporter probes respectively comprising SEQ ID NO:5 and 7. The kit of any preceding aspect or embodiment may further comprise a primer pair for amplifying a normalizing gene.

In a ninth aspect, the invention relates to the use of one or more primer sets specific for clonally rearranged IGH genes in a method for determining whether a plasma or serum sample derived from a blood sample is contaminated with cfDNA from B lymphocytes lysed in the process of preparing the plasma or serum sample from the blood sample.

In further aspects and embodiments, the invention relates to methods of diagnosing or prognosing a subject at risk for or suffering from cancer, and to methods of monitoring the treatment of a subject suffering from cancer, which comprise the methods, kits or uses of any preceding aspects or embodiments.

Definitions

"Cell-free DNA" or "cfDNA" herein refers to DNA that exists outside a cell in a subject or the isolated form of such DNA, typically in a body fluid. Unless otherwise indicated or contrary to context, "circulating DNA" herein refers to cfDNA present in blood.

As used herein, a "subject" refers to a human or animal, including all mammals such as primates (particularly higher primates), sheep, dog, rodents (e.g., mouse or rat), guinea pig, goat, pig, cat, rabbit, and cow. In one embodiment, the subject is a human. In one embodiment, the subject has a condition associated with elevated cfDNA levels in blood, e.g., cancer, pregnancy, inflammation, exercise-induced inflammation, or the like. In a particular embodiment, the subject is suffering from or at risk for a disease or disorder, such as, e.g., cancer. In one embodiment, the subject is an experimental animal or animal suitable as a model for a condition associated with elevated cfDNA levels in blood.

As used herein, "cancer" refers to a disease or disorder characterized by uncontrolled division of cells and the ability of these cells to spread, either by direct growth into adjacent tissue through invasion, or by implantation into distant sites by metastasis. Since the present invention relates to the detection of B cell DNA as an indication of cfDNA contamination of a body fluid sample, it should not normally be applied to cancers of B cell origin (e.g. B-cell lymphoma, acute lymphoblastic leukemia, chronic lymphocytic leukemia and multiple myeloma), which are thereby specifically excluded. Exemplary cancers categorized by the type of cells the cancer cells most resemble and/or originate from include, but are not limited to, carcinoma, sarcoma, mesothelioma, glioma and germinoma. Exemplary cancers categorized by the organ or body part the cancer cells originate from include, but are not limited to, colorectal cancer, prostate cancer, lung cancer, breast cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, liver cancer, esophageal cancer, gastric cancer, intestinal cancer, colon cancer, rectal cancer, neuroblastoma, and retinoblastoma. Preferably, the cancer is colorectal cancer, melanoma, thyroid cancer, lung cancer, prostate cancer, breast cancer, ovarian cancer, pancreatic cancer or liver cancer.

The term "body fluid" refers to any body fluid in which cfDNA may be present, including, without limitation, whole blood, serum, plasma, bone marrow, cerebral spinal fluid, peritoneal/pleural fluid, lymph fluid, ascite, serous fluid, sputum, lacrimal fluid, stool, and urine. Typically, the body fluid to be analyzed according to the invention is derived from a sample of whole blood (i.e., a blood sample comprising both blood cells and plasma). Preferably, the body fluid is plasma or serum.

As used herein, "quantitative Polymerase Chain Reaction" or "qPCR", also known as "real-time quantitative PCR" or "Q-PCR", refers to the well-known PCR technique which can be used to amplify and simultaneously quantify one or more target DNA molecules. The quantity can be converted to either an absolute number of copies or a relative amount when normalized to DNA input or additional normalizing genes. "Multiplex qPCR" refers to the simultaneous detection of several target DNA molecules, either by using degenerate primers or several primer pairs. Such methods and their applications in analyzing and/or quantifying DNA in different types of samples are well known in the art and described in, e.g., "Real-time PCR (Advanced Methods)" M Tevfik Dorak (Editor) 2006 by Taylor & Francis Group ISBN: 0-4153-7734-X.

As used herein, a "normalizing gene," also known as "reference gene" in the art, is when referring to DNA, a gene sequence whose number of copies, genome equivalents and/or alleles per cell or cell equivalent are assumed constant between different samples. The level of normalizing gene in e.g. a plasma or serum sample can thus be used to measure or estimate the number of DNA alleles in a sample or to normalize the determined level of target gene, e.g., a mutated cancer gene in the sample so that different samples can be compared more reliably. Many standard normalizing genes are known and used in the art of qPCR analysis of tissue DNA (see, e.g., Bondo Dydensborg et al., Am J Physiol Gastrointest Liver Physiol 2006; 290:G1067-G1074 and WO 2006138443 A2). Normalizing genes suitable for cfDNA analysis in cancer include, but are not limited to, beta-2-microglobulin (B2M), GAPDH, ACTIN and cyclophilin.

A "reporter probe", as used herein, refers to a DNA probe with a directly or indirectly detectable "reporter" molecule at one end and a quencher of the detectable molecule at the opposite end of the probe, known and used in qPCR procedures. Typically, the close proximity of the reporter to the quencher prevents detection of the reporter, but breakdown of the probe by the 5' to 3' exonuclease activity of the Taq polymerase breaks the reporter-quencher proximity and thus allows the reporter to be detected. An increase in the product (the target gene) targeted by the reporter probe at each PCR cycle therefore causes a proportional increase in the detectable signal. The reporter can be, e.g., a luminescent, fluorescent, phosphorescent or otherwise directly or indirectly detectable molecule.

Specific Embodiments of the Invention

Various methods are know for detection and quantification of cfDNA, including qPCR-based methods, UV-spectrophotometry, chemiluminescense methods, and mass spectrometry (MALDI-TOF). cfDNA analyses based on qPCR are particularly advantageous, in that they are highly sensitive and specific for cfDNA in contrast to e.g. UV-spectophotometry, where also RNA and protein are measured.

Body fluid samples for cfDNA analysis can be obtained from a subject using any of the methods known in the art. Methods for extracting cfDNA from body fluid samples are also well-known in the art (see, for example Jung et al., Clinica Chimica Acta 411 (2010) 1611-1624, and Messaoudi et al., Clinica Chimica Acta 2013; 424:222-230). For example, cfDNA in a body fluid sample such as, e.g., blood, can be separated from cells present in the body fluid by, e.g., centrifugation, and then precipitated in alcohol or otherwise purified from the remaining fraction, and dissolved in an aqueous, optionally buffered, solution. Most preferably, commercially available standard equipment and kits for purifying DNA from body fluids are employed. Exemplary equipment and kits are described in the Examples. The preferred type of body fluid is derived from blood, such as serum and plasma.

The present invention then utilizes a PCR assay for identifying and/or quantifying B cell DNA contamination in the body fluid sample, advantageously qPCR, to investigate whether the sample is suitable for cfDNA analysis. The PCR can be a single (monoplex) or a multiplex PCR. In a preferred embodiment, a set of primers according to the invention is used in a standardized multiplex PCR assay, using for example two or more forward primers, or three or four forward primers, together with one or more reverse primer(s) and, optionally, one or more reporter probes. The primers and optional reporter probes are at least specific for rearranged IGH genes, rearranged IGK and/or rearranged IGL genes. However, primers for one or more normalizing genes, tumor marker genes, and internal control genes can also be included in the methods and kits of the invention.

Recombination of the IgH locus is the earliest step in the generation of the mature antibody repertoire in B lymphocytes. The IgH locus is large, covering a region of 3 Mb, and highly complex, containing approximately 44 variable (V) genes, 27 diversity (D) genes, and 6 joining (J) genes. The V-D-J rearrangements are mediated by a recombinase enzyme complex. In B cell differentiation, the IGH genes rearrange first, followed by IGK deletion and IGL rearrangement. Similar principles apply for the T-cell receptor (TCR) in T cells. Since, in principle, all cells of a lymphoid malignancy have a common clonal cell of origin, PCR primers and protocols for detecting clonal immunoglobulin or TCR gene rearrangements have been developed as diagnostic tool for lymphoid malignancies of T- or B-cell origin. The selection of primers and their application for such purposes are described in the Examples and in, e.g., van Dongen et al. (2003), van der Velden et al. (2006), van der Velden et al. (2007), WO1997046706A1, WO 2005054506 A2, WO 2004/033728 A2 and WO 2013128204 A1, each of which incorporated by reference in its entirety, including the description and sequences of all IGH, IGL and/or IGK primer sequences therein.

Suitable primers sets for the methods, kits and uses of the invention can also be designed and identified according to the methods described in the Examples. Specifically, the DNA sequences for immunoglobulin genes are available in public databases such as, e.g., the IMGT/V-QUEST reference directory website (http://www.imgt.org/vquest/refseqh.html). Using such DNA sequences, segments suitable for primer targeting can be identified by aligning all or at least a subset of the IGHV-genes, IGKV-genes or IGLV genes, and then selecting highly conserved regions, using standard sequence alignment software. Typically, a primer suitable for qPCR comprises between about 10 and about 30, such as between about 15 and about 25, such as between about 17 and about 23 nucleotide bases. Primer sets for mono- or multiplex PCR can then be designed by testing different combinations of primers on DNA from whole blood, selecting those that reproducibly give rise to a PCR product, preferably with a "low" number of PCR cycles which indicates (1) an efficient amplification and (2) that the primer targets a number of rearranged IGH genes. Degenerate versions of a specific primer sequence can also be prepared so that the primer set comprises 2, 3 or 4 variants of the primer sequence where the nucleotide at a specific position is varied between some or all nucleotide bases (i.e., A, C, T and G), allowing for the most optimally "matched" primer to bind a specific target sequence. The target sequence for a primer is preferably unique, meaning that the sequence is not present within the remainder of the genome. This arrangement prevents other sequences being incorrectly identified by the methods and kits of the invention.

In one embodiment, the primer set comprises one or more reverse primers specific for a unique region within one or more JH genes. Preferably, the one or more reverse primers are specific for a JH2 and/or JH5 gene segment. For example, the primer set may comprise a reverse primer sequence specific for a JH2 segment, a reverse primer sequence specific for a a JH5 segment, or two reverse primers specific for a JH2 and a JH5 segment, respectively. Most preferably, the primer set comprises a reverse primer comprising the sequence of SEQ ID NO:6 or a fragment or degenerate variant thereof, or SEQ ID NO:11 or a fragment or degenerate variant thereof. In one embodiment the reverse primer comprises the sequence of SEQ ID NO:6.

In one embodiment, the primer set comprises one or more forward primers specific for a unique region within one or more VH gene segments. Preferably, the one or more forward primers are specific for at least one of the VH1, VH3 and the VH4 gene segments. In one embodiment, the one or more forward primers comprise at least one primer specific for a VH3 gene segment. In one embodiment, the primer set comprises primers specific for VH1 and VH4 gene segments. In one preferred embodiment, the primer set comprises a forward primer comprising the sequence of SEQ ID NO:4 or a fragment or degenerate variant thereof. In another preferred embodiment, the primer set comprises a forward primer comprising the sequence of SEQ ID NO:14 or a fragment or degenerate variant thereof. In another preferred embodiment, the primer set comprises forward primers comprising the sequences of SEQ ID NO:12 and 15, respectively, or fragments or degenerate variants thereof. In another preferred embodiment, the primer set comprises a forward primer comprising the sequence of SEQ ID NO:4.

In another preferred embodiment, the primer set comprises at least three forward primers comprising the sequences of SEQ ID NOS:12, 14 and 15, respectively.

Specific primer sets can then be selected and tested as described in Example 1 and 2. Preferably, the primer set comprises nucleic acid amplification primers capable of amplifying a VH-JH IGH rearrangement comprising a forward primer and a reverse primer, wherein said forward primer is specific for a VH3 gene segment and the reverse primer is specific for a JH or JH segment. For example, the primer set can comprise a forward primer specific for a VH3 gene segment and a reverse primer specific for a JH2 or JH5 gene segment. In one embodiment, the primer set comprises a forward primer comprising SEQ ID NO:4 or a degenerate variant thereof, and a reverse primer comprising SEQ ID NO:6 or a degenerate variant thereof. This primer set is herein referred to as "PBC". In one embodiment, the primer set comprises a forward primer comprising SEQ ID NO:14 or a degenerate variant thereof, and a reverse primer comprising SEQ ID NO:11 or a degenerate variant thereof. In one embodiment, the primer set comprises forward primers comprising the sequences of SEQ ID NOS:12 and 15, respectively, or degenerate variants thereof, and a reverse primer comprising the sequence of SEQ ID NO:11 or a degenerate variant thereof. For example, the primer set may comprise forward primers comprising SEQ ID NOS:12, 14 and 15, respectively, or degenerate variants of any thereof, and a reverse primer comprising SEQ ID NO:11 or a degenerate variant thereof. This primer set is herein referred to as "VH134".

In one embodiment, the primer set additionally or alternatively comprises one or more nucleic acid amplification primers capable of amplifying a DH-JH IGH rearrangement, an IGK rearrangement and/or an IGL rearrangement. Suitable primer sets for amplifying IGK and/or IGL rearranged genes can be selected from the primers in Example 3. Additional primer sets are described in, e.g., van Dongen et al. (2003).

Additionally, one or more reporter probes binding to gene segments amplified by the primer sets of the invention can be employed in conjunction with qPCR. Typically, the probes have a length between about 15 and about 100 nucleotides, such as between about 20 and about 50 nucleotides, such as between about 25 and about 30 nucleotides, and are selected so as to be specific for the target and having a melting point approximately 10° C. higher than the forward and reverse primer. The probe is then modified to contain a 5'-reporter molecule (e.g., a dye such as FAM) and a 3'-quencher molecule (e.g. a dye such as TAMRA). Preferred probes are those comprising SEQ ID NO:5, SEQ ID NO:7, or fragments or degenerate variants thereof. In one embodiment, a reporter probe comprising the sequence of SEQ ID NO:5 is used in conjunction with the PBC primer set. In one embodiment, a reporter probe comprising the sequence of SEQ ID NO:7 is used in conjunction with the VH134 primer set.

It will be appreciated that conducting monoplex or multiplex qPCR assays using these primers and probes are readily apparent to the skilled person in accordance with standard molecular biology and PCR techniques. In a typical PCR reaction, the set up includes a buffer containing at least one thermostable DNA polymerase (such as Taq polymerase), specific primers for the DNA of interest, deoxynucleotides, and any salts or other components that are desired. The DNA is typically denatured by heating to separate the two strands. The sample is then cooled to e.g. about 50° C. to 60° C., during which the specific primers specifically hybridize to complementary sequences on the target DNA. Amplification of the target DNA is then accomplished by extension of the primers by the thermostable polymerase at about 72° C. After extension of the primers, the resulting mixture is heated at greater than about 90° C. to denature double-stranded products, and the process of primer annealing and extension is repeated. Cycles of annealing, extending, and denaturation are performed at least until a detectable amount of product is produced, and typically between 25 and 35 cycles are performed.

For qPCR, the amplified DNA is detected as the reaction progresses in "real time", e.g. by the use of one or more reporter probes as described above, leading to a detectable signal reflecting the number of copies formed of the target gene, i.e., the allele copy number. For example, if a multiplex qPCR reaction is conducted with primers for IGH, IGK and/or IGL rearranged genes as well as for one or more of a normalizing gene, tumor marker and control gene fragment, typically, one type of reporter molecule is used for the B cell-specific genes and other, different types of reporter molecules are used for each of the normalizing gene and tumor marker, so as to allow their separate detection and quantification.

The detection of amplified sequences comprising B cell rearrangements then indicates the presence of contaminating cellular DNA from cells lysed during or after the taking of the blood or other body fluid sample. Whether the sample is then determined to be unsuitable for cfDNA analysis and thus excluded can depend on the level of contamination and the level of cfDNA. Typically, the body fluid sample is determined to be unsuitable for cfDNA if the level of contaminating B cell DNA exceed a control value, optionally predetermined. The control value can be determined by the skilled person based on several considerations, including the purpose of the cfDNA analysis, the subject in question, the (disease) condition studied, the level of cfDNA in one or more normal control subjects (from actual control tests and/or literature), and the relative level of B cell DNA compared to the measured or predicted level of cfDNA and/or normalizing gene. As shown in Example 1, the average level of the normalizing gene B2M in normal subjects was in the range 3000-5000 allele copy numbers per ml plasma whereas the level of contaminant B cell DNA ranged from 0 to 36000 allele copy numbers. In cancer patients, the level of cfDNA may be in the order of a 1000-fold higher. So, if the purpose of the analysis is to study the level of cfDNA in a condition associated with only a small increase in cfDNA (e.g., exercise-induced inflammation), even a minor contamination with B cell DNA can affect the results so the absolute level of contamination, i.e., the control value, should then be low. In cancer patients, the level of cfDNA may be in the order of a 1000-fold higher, so a control value for B cell contamination can then also be set higher. The skilled person can select a suitable control value based on the design of the study or assay and/or the condition tested for or patient/subject group. The following provide some exemplary and non-limiting control values, which can be used as a general guide.

In one embodiment, the subject is not known to have a condition associated with significantly elevated cfDNA levels, and the control level is about 100 alleles or less of B cell DNA per mL body fluid, such as about 20 alleles or less, such as about 15 alleles or less, such as about 10 alleles or less, such as about 8 alleles or less, such as about 5 alleles or less, such as about 3 alleles or less, such as about 1 allele, per mL body fluid.

In one embodiment, the subject is known to have a condition associated with elevated cfDNA levels, and the control level can be about 1000 alleles or less of B cell DNA per mL body fluid, such as about 500 alleles or less, such as about 250 alleles or less, such as about 100 alleles or less, such as about 50 alleles or less, such as about 25 alleles or less, such as about 10 alleles or less, such as about 1 allele, per mL body fluid.

Alternatively, the control value can be a relative one as compared to the level of a normalizing gene, as described herein. In separate and specific embodiments, the control level is about 1% or less, such as about 0.5% or less, about 0.4% or less, about 0.3% or less, about 0.2% or less, about 0.1% or less, about 0.05% or less, or 0.01% or less of the actual or predicted level of the normalizing gene.

Once a body fluid sample has been determined to be unsuitable for cfDNA analysis because of contaminating B cell DNA, the sample can be excluded and optionally replaced with a new sample form the subject, purified from the contaminating DNA, or corrected for the contaminating DNA.

For example, since normal lymphocyte-derived DNA has a molecular size of at least 10000 bp (that is, unfragmented), whereas cancer cell-derived DNA is typically fragmented into smaller sizes. Accordingly, the lymphocyte-derived DNA can be removed from the plasma by utilizing this molecular size difference. The removal method may be any method known in the art which based on molecular size difference, including plasma filtration methods using membranes such as ultrafiltration membranes, microfiltration membranes or the like, or plasma filtration methods using migration in agarose or other gels.

As described above, the B cell contamination test of the invention can also comprise the detection or quantification of a tumor marker gene in the body fluid sample. Several genes have so far been identified as tumor markers for cfDNA analysis for the purpose of providing a diagnosis or prognosis of cancer in a subject suffering from or at risk for cancer, or to monitor treatment of a subject suffering of cancer. Exemplary tumor marker genes include, but are not limited to, KRAS and BRAF and p53 (carcinomas such as, e.g., colorectal, pancreatic cancer (KRAS), melanoma (BRAF), breast cancer (PIK3CA), lung cancer (EGFR and EML4-ALK), prostate cancer (TMPRSS2:ERG) (e.g., Spindler et al., Clin Cancer Res 2012; 18:1177-1185). Associated primers and PCR methodologies for tumor marker gene detection in body fluid cfDNA are described in, e.g., WO 2012/028746 A1.

In one aspect, the invention provides for the use of the method or primer sets of any preceding aspect or embodiment in a method for diagnosing cancer in a subject using cfDNA analysis of a body fluid sample derived from blood, wherein the presence of contaminating B cell DNA in the body fluid sample is determined.

In one aspect, the invention provides for the use of the method or primer set(s) of any preceding aspect or embodiment in a method for providing a prognosis for a cancer in a subject using cfDNA analysis of a body fluid sample derived from blood, wherein the presence of contaminating B cell DNA in the body fluid sample is determined.

In one aspect, the invention provides for the use of the method or primer set(s) of any preceding aspect or embodiment in a method for providing a prognosis for a cancer in a subject using cfDNA analysis of a body fluid sample derived from blood, wherein the presence of contaminating B cell DNA in the body fluid sample is determined.

In one aspect, the invention provides for the use of the method of primer set of any preceding aspect or embodiment in a method for monitoring treatment of a cancer in a subject using cfDNA analysis of a body fluid sample derived from blood, wherein the presence of contaminating B cell DNA in the body fluid sample is determined.

The invention also provides kits comprising a PCR primer set for amplifying one or more of clonally rearranged IGH genes, IGK genes and IGL genes, typically at least IGH genes, in the sample. In one embodiment, the kit comprises any one or more of the primers or primer sets described in a preceding aspect or embodiment, and optionally at least one, two, three or all of a reporter probe, a DNA polymerase, a buffer and a set of dNTPs. The kit can also contain instructions for its use in PCR determination of B cell contamination of a body fluid.

In one embodiment, kit comprises one or more reverse primers specific for a unique region within one or more JH genes. Preferably, the one or more reverse primers are specific for a JH2 and/or JH5 gene segment. For example, the primer set may comprise a reverse primer sequence specific for a JH2 segment, a reverse primer sequence specific for a JH5 segment, or two reverse primers specific for a JH2 and a JH5 segment, respectively. Most preferably, the primer set comprises a reverse primer comprising the sequence of SEQ ID NO:6 or a fragment or degenerate variant thereof, or SEQ ID NO:11 or a fragment or degenerate variant thereof. In one embodiment the reverse primer comprises the sequence of SEQ ID NO:6.

In one embodiment, kit comprises one or more forward primers specific for a unique region within one or more VH gene segments. Preferably, the one or more forward primers are specific for at least one of the VH1, VH3 and the VH4 gene segments. In one embodiment, the one or more forward primers comprise at least one primer specific for a VH3 gene segment. In one embodiment, the primer set comprises primers specific for VH1 and VH4 gene segments. In one preferred embodiment, the primer set comprises a forward primer comprising the sequence of SEQ ID NO:4 or a fragment or degenerate variant thereof. In another preferred embodiment, the primer set comprises a forward primer comprising the sequence of SEQ ID NO:14 or a fragment or degenerate variant thereof. In another preferred embodiment, the primer set comprises forward primers comprising the sequences of SEQ ID NO:12 and 15, respectively, or fragments or degenerate variants thereof. In another preferred embodiment, the primer set comprises a forward primer comprising the sequence of SEQ ID NO:4. In another preferred embodiment, the primer set comprises at least three forward primers comprising the sequences of SEQ ID NOS:12, 14 and 15, respectively.

Preferably, the kit comprises a primer set capable of amplifying a VH-JH IGH rearrangement comprising a forward primer and a reverse primer, wherein said forward primer is specific for a VH3 gene segment and the reverse primer is specific for a JH2 or JH5 segment. For example, the primer set can comprise a forward primer specific for a VH3 gene segment and a reverse primer specific for a JH2 or JH5 gene segment. In one embodiment, the primer set comprises a forward primer comprising SEQ ID NO:4 or a degenerate variant thereof, and a reverse primer comprising SEQ ID NO:6 or a degenerate variant thereof. This primer set is herein referred to as "PBC". In one embodiment, the primer set comprises a forward primer comprising SEQ ID NO:14 or a degenerate variant thereof, and a reverse primer comprising SEQ ID NO:11 or a degenerate variant thereof. In one embodiment, the primer set comprises forward primers comprising the sequences of SEQ ID NOS:12 and 15, respectively, or degenerate variants thereof, and a reverse primer comprising the sequence of SEQ ID NO:11 or a degenerate variant thereof. For example, the primer set may comprise forward primers comprising SEQ ID NOS:12, 14 and 15, respectively, or degenerate variants of any thereof, and a reverse primer comprising SEQ ID NO:11 or a degenerate variant thereof. This primer set is herein referred to as "VH134".

The kit may additionally or alternatively comprise one or more nucleic acid amplification primers capable of amplifying a DH-JH IGH rearrangement, an IGK rearrangement and/or an IGL rearrangement. Suitable primer sets for amplifying IGK and/or IGL rearranged genes can be selected from the primers in Example 3. Additional primer sets are described in, e.g., van Dongen et al. (2003).

The kit may also comprise one or more reporter probes binding to gene segments amplified by the primer sets of the kit for use in conjunction with qPCR. Typically, the probes have a length between about 15 and about 100 nucleotides, such as between about 20 and about 50 nucleotides, such as between about 25 and about 30 nucleotides, and are selected so as to be specific for the target and having a melting point approximately 10° C. higher than the forward and reverse primer. Preferred probes are those comprising SEQ ID NO:5, SEQ ID NO:7, or fragments or degenerate variants thereof. In one embodiment, a reporter probe comprising the sequence of SEQ ID NO:5 is used in conjunction with the PBC primer set. In one embodiment, a reporter probe comprising the sequence of SEQ ID NO:7 is used in conjunction with the VH134 primer set.

In one aspect, the invention provides for the use of any such kit in a method for determining the suitability of a body fluid sample such as, e.g., plasma or serum, for cfDNA analysis.

In one aspect, the invention provides for the use of any such kit in a method for determining whether a body fluid sample such as, e.g., plasma or serum, is contaminated with DNA derived from B lymphocytes in the body fluid sample.

In one aspect, the method, kit or use of any preceding aspect or embodiment further comprises primers and, optionally, reporter probes for one or more tumor marker genes.

In one aspect, the invention provides for the use of any such kit in a method for diagnosing cancer in a subject using cfDNA analysis of a body fluid sample derived from blood, wherein the presence of contaminating B cell DNA in the body fluid sample is determined.

In one aspect, the invention provides for the use of any such kit in a method for providing a prognosis for a cancer in a subject using cfDNA analysis of a body fluid sample derived from blood, wherein the presence of contaminating B cell DNA in the body fluid sample is determined.

In one aspect, the invention provides for the use of any such kit in a method for providing a prognosis for a cancer in a subject using cfDNA analysis of a body fluid sample derived from blood, wherein the presence of contaminating B cell DNA in the body fluid sample is determined.

In one aspect, the invention provides for the use of any such kit in a method for monitoring treatment of a cancer in a subject using cfDNA analysis of a body fluid sample derived from blood, wherein the presence of contaminating B cell DNA in the body fluid sample is determined.

Each Example below is intended to illustrate, but not to limit, the scope of the invention. Other procedures, materials or applications known to those skilled in the art may alternatively be utilized. Indeed, those of ordinary skill in the art can readily envision and produce further embodiments, based on the teachings herein, without undue experimentation.

Example 1

Quantification of Cell Free DNA and Detection of B Cell DNA in Plasma

Plasma was obtained from 9 ml EDTA-blood samples by centrifugation at 2000 g for 10 min within 2 hour and stored at −80° C. until use. DNA was purified from 1.2 ml plasma samples using a QIAsymphony virus/bacteria midi-kit on a QIAsymphony robot (Qiagen) according to the manufacturer's instructions. DNA was eluted in volume of 110 μL in the supplied buffer.

DNA was purified from 200 μL whole blood using a Maxwell 16 Blood DNA purification kit on a Maxwell 16 purification robot (Promega) according to the manufacturer's instructions. The DNA was eluted in 300 μL.

The number of genomic DNA alleles was qualified by real time quantitative PCR (qPCR) using a primer set for the beta-2-microglobulin gene (B2M) with an amplicon size of 102 base pairs:

```
Forward primer:
                                           (SEQ ID NO: 1)
TAAAACTTAATGTCTTCCTTTTTTTCTC Probe:
                                           (SEQ ID NO: 2)
Fam-CCTCCATGATGCTGCTTACATGTCTC-Tamra Reverse primer:
                                           (SEQ ID NO: 3)
AAACATTTTCTCAAGGTCAAAAACTTA
```

To detect and quantify DNA derived from whole blood cells the IgH rearrangements of B cells were used. To detect a fraction of the DNA derived from blood B-cells qPCR primers and probes were designed using DNA sequence alignments of the VH segment and the JH segment of the immunoglobulin genes. The DNA sequences for the immunoglobulin genes were obtained from the IMGT/V-QUEST reference directory sets (http://www.imgt.org/vquest/refseqh.html) database and sequence alignment performed using the CLC workbench software (CLC Bio, Denmark). Several primer set were designed and tested and a set (PBC) that gave the most consistent result was selected:

```
Forward:
                                           (SEQ ID NO: 4)
ATCTGCAAATGAACAGYCTGAGA Probe:
                                           (SEQ ID NO: 5)
Fam-CYGAGGACACRGCTGTGTATTACTGTGC-Tamra Reverse:
                                           (SEQ ID NO: 6)
CTTACCTGAGGAGACGGTGAC
```

"Y" represents C or T, while "R" represents A or G.

The forward primer targets the coding region of the IGVH3 gene, the probe is specific for a downstream segment of the IGHV3 gene, and the reverse primer targets the coding region of the IGJH2 gene, using the terminology of the IMGT/V-QUEST reference database.

The B2M and PBC qPCR reactions were run in parallel in triplicates in a volume of 25 μL with 5 μL of plasma DNA per reaction using ABI Universal Mastermix with UNG (Applied Biosystems) and performed on an ABI Prism7900HT (Applied Biosystems, Foster City, Calif.). The qPCR reaction conditions were: 2 min at 50 degrees Celsius (C) and 10 min at 95 degrees C., followed by 50 cycles of 15 s at 95 degrees C. and 60 s at 60 degrees C.

To determine the fraction of whole blood DNA (i.e., whether present as cellular DNA or a cfDNA) detected by the PBC primer set, whole blood DNA from 76 normal donors was purified and analyzed by qPCR using the B2M and PBC primer sets. The results are shown in FIG. 2. The average ratio between alleles (DNA copy number) and the fraction of rearranged IgH alleles detected was calculated to 260. The fraction of B cell DNA detected in normal blood samples was in average 0.4%.

The number of DNA alleles per ml of plasma in 100 normal donors was determined by qPCR using the B2M primer set, and B lymphocyte DNA contamination determined using the PBC primer set. The results are shown in FIG. 3. Seven plasma samples were determined to be contaminated with lymphocyte DNA (n=7), respectively containing 27, 37000, 310, 42, 23, 7 and 100 alleles per ml. Also shown in FIG. 3 is the normalized number of genomic alleles, obtained by dividing the number of total (B2M) alleles with number of PBC alleles. The normalized B2M/PBC values provide an estimate of the degree of contaminating lymphocyte DNA. It was observed that a contamination with more than 100 copies of B cell DNA per mL had an significant effect on the cfDNA allele number.

Discussion

The above test on whole blood was carried out to show the fraction of DNA detected by the PBC in normal blood samples, as well as the variation between the individual samples. The variation between the subjects could likely be ascribed to a combination of the genetic background and the infection history of each individual. This should be considered when using the PBC to normalize a sample with contaminating lymphocyte DNA. However, by also detecting rearranged IGL or IGK genes, a more quantitative determination may be possible.

When preparing the 100 plasma samples from normal individuals, great care was taken during the sampling and pipetting to avoid the plasma being contaminated with lymphocyte DNA. Nonetheless, it was observed that 7 samples were contaminated. Especially one sample was heavily contaminated and would have resulted in a misinterpretation in a clinical setting.

Example 2

Selection of Additional Primers and Probes for Identification of B Cell IgH Rearrangements Sequences of the JH-genes including a 3' downstream non-coding region were aligned using the CLC Genomic workbench software (CLC Bio, Aarhus, Denmark). From the alignment a consensus TaqMan probe (Fam-ACCCTG-GTCACCGTCTCCTCAGGTG-Tamra (SEQ ID NO:7) was designed detecting the coding region of the IGHJ1, IGHJ2, IGHJ4 and IGHJ5 genes.

Reverse primers adjacent to the probe located downstream in the non-coding region were designed for the 4 IGHJ-genes:

RJH1
(SEQ ID NO: 8)
CGCTATCCCCAGACAGCAGA

RJH2
(SEQ ID NO: 9)
GGTGCCTGGACAGAGAAGACT

RJH4
(SEQ ID NO: 10)
CAGAGTTAAAGCAGGAGAGAGGTTGT

RJH5
(SEQ ID NO: 11)
AGAGAGGGGGTGGTGAGGACT

From alignments, forward primers from the consensus of the IGHV1-7 gene families were designed:

VH1
(SEQ ID NO: 12)
GAGCTGAGCAGCCTGAGATCTGA

VH2
(SEQ ID NO: 13)
CAATGACCAACATGGACCCTGTGGA

VH3
(SEQ ID NO: 14)
TCTGCAAATGAACAGCCTGAGAGCC

VH4
(SEQ ID NO: 15)
GCTCTGTGACCGCCGCGGA

VH5
(SEQ ID NO: 16)
CAGCACCGCCTACCTGCAGTGGAGC

VH6
(SEQ ID NO: 17)
GTTCTCCCTGCAGCTGAACTCTGTG

VH7
(SEQ ID NO: 18)
AGCACGGCATATCTGCAGATCAG

To test the functionality combined with the gene usage, 11 multiplex primer sets were assembled and tested on normal donor DNA from whole blood: Four sets with all the 7 forward primers, the probe and one of the reverse primers and 7 sets with one of the 7 forward primers, the probe and all 4 reverse primers.

From the testing it was seen that only primer sets with the reverse primer RJH5 (SEQ ID NO:11) and with the forward primers VH1, VH3 or VH4 (SEQ ID NOS:12, 14 and 15, respectively) were functional, resulting in a PCR product. The highest PCR target copy number was seen with the VH3 forward primer consistent with the IGHV3 gene family being very large.

From the primer testing 2 multiplex primer sets were assembled:

| Assay | Primer | Sequence | Conc. in nM |
|---|---|---|---|
| VH134 | VH1 | GAGCTGAGCAGCCTGAGATCTGA | 300 |
| | VH3 | TCTGCAAATGAACAGCCTGAGAGCC | 300 |
| | VH4 | GCTCTGTGACCGCCGCGGA | 300 |
| | T-JH1245 | Fam-ACCCTGGTCACCGTCTCCTCAGGTG-Tamra | 200 |
| | RJH4 | CAGAGTTAAAGCAGGAGAGAGGTTGT | 600 |
| | | | |
| VH14 | VH1 | GAGCTGAGCAGCCTGAGATCTGA | 300 |
| | VH4 | GCTCTGTGACCGCCGCGGA | 300 |
| | T-JH1245 | Fam-ACCCTGGTCACCGTCTCCTCAGGTG-Tamra | 200 |
| | RJH4 | CAGAGTTAAAGCAGGAGAGAGGTTGT | 600 |

The 2 assay were further tested on 10 normal donor DNA samples from whole blood and the VH134 assay generally gave a 1-4 fold better amplification that the VH14 primer set.

Example 3

Selection of additional primers and probes for identification of B cell IGK and IGL rearrangements Primers for Amplifying IGK Rearrangements:

Sequences of the IGKV1- and IGKV2-genes were aligned using the CLC Genomic workbench software (CLC Bio, Aarhus, Denmark). From the alignment, two consensus TaqMan probes IGKV1p
(SEQ ID NO: 19)
Fam-CAGCCTGCAGCCTGAAGATTTTGCA-Tamra IGKV2p
(SEQ ID NO: 20)
Fam-ATGCTGAGGATGTTGGGGTTTATTG-Tamra were designed detecting the coding region of the IGKV1 and IGKV2. Reverse primer adjacent to the probe located downstream in the coding region was designed for the IGKJ1 to 4 genes:

IGKJ14
(SEQ ID NO: 21)
TTTGATCTCCACCTTGGTCC

From alignments, forward primers from the consensus of the IGKV1 and IGKV2 gene families were designed:

IGKV1
(SEQ ID NO: 22)
GGACAGATTTCACTCTCACCAT

IGKV2
(SEQ ID NO: 23)
CATGCTGAAATCAGGAGGAT

To test the functionality combined with the gene usage, multiplex primer sets are assembled and tested on normal donor DNA from whole blood. Sets that are functional, resulting in a PCR product are selected.

Primers for Amplifying IGL Rearrangments:

Sequences of the IGLV1 and IGLV2-gene family were aligned using the CLC Genomic workbench software (CLC Bio, Aarhus, Denmark). From the alignment, a consensus TaqMan probe IGKV12p Fam-TGCCAGTCCTATRACA-GCAGCCT-Tamra (SEQ ID NO:24) was designed detecting the coding region of the IGV1-gene family.

Sequences of the IGLJ1 to 6 genes were aligned using the CLC Genomic workbench software (CLC Bio, Aarhus, Denmark). From the alignment, a consensus reverse primer was designed:

IGKL16
(SEQ ID NO: 25)
CTAGGACGGTCAGCTTGGT

From alignments, forward primer from the consensus of the IGLV1 and IGLV2 gene families were designed:

IGLV1
(SEQ ID NO: 26)
GGCTGRGGATGAGGCYAATTATT

IGLV2
(SEQ ID NO: 27)
GGCTGRGGATGAGGCYGATTATT

"Y" represents C or T, while "R" represents A or G.

To test the functionality combined with the gene usage, primer sets are assembled and tested on normal donor DNA from whole blood. Sets that are functional, resulting in a PCR product are selected.

Example 4

To demonstrate the ability of the PBC primer set to detect contaminating lymphocyte DNA in plasma samples, spike-in experiments were performed. Plasma was spiked with a whole blood sample in 3.3 fold increments from 0.1 µL to 1000 µL keeping the final volume constant of 1200 µL. A 182 base pair exogenious internal CPP1 control DNA fragment was added to all samples. Purified DNA was analysed by qPCR using the B2M, PBC and CPP1 primer set and the number of alleles per mL calculated and plotted as shown in FIG. 4.

The PBC primer set detected a few DNA alleles in the pure plasma sample (marked 0), indicating that the plasma pool used was slightly contaminated with lymphocyte DNA. From FIG. 4 it can be seen from the increase in PBC alleles that a contamination of 0.3 µL of whole blood can be detected. However, a contamination of 1 to 3 µL of whole blood is needed before it has an effect on the number of cell free DNA alleles in the plasma measured by the B2M primer set. From 3 µL of whole blood spike-in, the number of PBC alleles parallels that of B2M, indicating that the DNA detected is from lymphocytes. At the highest concentration where 1000 µL of whole blood was added, a decrease in the exogenous CPP1 can be seen, indicating that the purification system was overloaded and DNA lost.

REFERENCES

Jahr et al., Cancer Research 2001; 61:1659-1665
Van der Velden et al., Leukemia 2007; 21:604-11.
Van der Velden et al., Haematologica 2006; 91:679-982.
Van Dongen et al., Leukemia 2003; 17:2257-2317.
Ivancic-Jelecki et al., Journal of Chromatography A 2009; 1216:2717-2724.
Fleischhacker et al., Biochimica et Biophysica Acta 2007; 1775:181-232.
Schwarz et al., Annals of Hematology 2009; 88(9):897-905.
EP 1712639 B1
US 2010/0124743 A1
US 2013/0012405 A1
WO 2006/128192 A1
WO 1997/046706 A1
WO 2004/033728 A2
WO 2005/054506 A2
WO 2013/128204 A1
WO 2011051495 A1

The invention claimed is:

1. A method of determining whether a body fluid sample derived from a blood sample from a subject, who is not suffering from a cancer of B cell origin, is suitable for quantifying cell-free DNA (cfDNA), comprising
   (a) performing a quantitative Polymerase Chain Reaction (qPCR) on a body fluid sample derived from a blood sample to determine a level of clonally rearranged genes selected from immunoglobulin heavy-chain (IGH) genes, immunoglobulin kappa (IGK) genes, immunoglobulin lambda (IGL) genes, and a combination of any thereof; and
   (b) identifying the body fluid sample as unsuitable for quantifying cfDNA if the level of clonally rearranged genes exceeds a control value,
   wherein the qPCR is performed with at least one primer pair selected from
   (i) SEQ ID NOS: 4 and 6,
   (ii) SEQ ID NOS:15 and 11,
   (iii) SEQ ID NOS: 12 and 11,
   (iv) SEQ ID NOS:14 and 11,
   (v) a combination of (ii) to (iv), and
   (vi) a combination of any two or more of (i) to (iv).

2. The method of claim 1, wherein the qPCR is performed with primer pairs comprising SEQ ID NOS: 4 and 6.

3. The method of claim 1, wherein the body fluid is plasma.

4. The method of claim 1, wherein the body fluid is serum.

5. A method of evaluating whether a body fluid sample derived from a blood sample from a subject, who is not suffering from a cancer of B cell origin, is contaminated with cfDNA from B lymphocytes lysed in the blood sample, comprising
   (a) performing a quantitative Polymerase Chain Reaction (qPCR) on a body fluid sample derived from a blood sample to determine a level of clonally rearranged genes selected from IGH genes, IGK genes, IGL genes, and a combination of any thereof; and (b) identifying the body fluid sample as contaminated with cfDNA from B lymphocytes if the level of clonally rearranged genes exceeds a control value, wherein the qPCR is performed with at least one primer pair selected from (vii) SEQ ID NOS: 4 and 6,
(viii) SEQ ID NOS: 15 and 11,
(ix) SEQ ID NOS: 12 and 11,
(x) SEQ ID NOS: 14 and 11,
(xi) a combination of (ii) to (iv), and
(xii) a combination of any two or more of (i) to (iv).

6. The method of claim 5, wherein the qPCR is performed with primer pairs comprising SEQ ID NOS: 4 and 6.

7. The method of claim 5, wherein the body fluid is plasma.

8. The method of claim 5, wherein the body fluid is serum.

* * * * *